United States Patent [19]

Inoue et al.

[11] Patent Number: 5,296,246
[45] Date of Patent: Mar. 22, 1994

[54] ACTIVE AMINO ACID CA, BEVERAGES CONTAINING SAME, AND PROCESS FOR THEIR PRODUCTION

[75] Inventors: Ranko Inoue; Kohzo Yamamoto, both of Tokyo, Japan

[73] Assignee: Fujix Corporation, Tokyo, Japan

[21] Appl. No.: 925,767

[22] Filed: Aug. 7, 1992

[30] Foreign Application Priority Data

Aug. 9, 1991 [JP] Japan .................. 3-200851

[51] Int. Cl.$^5$ .................................. A23L 1/304
[52] U.S. Cl. ........................ 426/74; 426/590; 426/656
[58] Field of Search ................... 426/74, 656, 590

[56] References Cited

U.S. PATENT DOCUMENTS

| | | | |
|---|---|---|---|
| 3,931,416 | 1/1976 | Grams | 426/74 |
| 4,027,043 | 5/1977 | Schroeder | 426/74 |
| 4,267,197 | 5/1981 | Sawhill | 426/74 |
| 4,540,584 | 9/1985 | Someya | 426/74 |
| 4,560,561 | 12/1985 | Henderson | 426/454 |
| 4,684,529 | 8/1987 | Ueno | 426/244 |
| 4,711,897 | 12/1987 | Lindsey | 426/2 |
| 4,851,242 | 7/1989 | Dubois | 426/74 |
| 4,994,284 | 2/1991 | Miller | 426/74 |
| 5,073,388 | 12/1991 | Miller | 426/74 |
| 5,108,767 | 4/1992 | Mulchandani | 426/74 |

FOREIGN PATENT DOCUMENTS

| | | | |
|---|---|---|---|
| 59-78650 | 5/1984 | Japan | 426/74 |

*Primary Examiner*—Carolyn Paden
*Attorney, Agent, or Firm*—Armstrong, Westerman, Hattori, McLeland & Naughton

[57] ABSTRACT

Active amino acid Ca, i.e., calcium oxide and/or hydroxide product coexistent with a slight amount of one or more amino acids and/or hydrolyzable amino acid derivatives is disclosed, which can be effectively absorbed into the human body and can deposit onto the bone with a high efficiency. Beverages containing same are also disclosed. The active amino acid Ca product is produced by calcining a calcium-containing material at 800°–980° C. in a calcining chamber free from oxygen, and subjecting the calcined product to a forced cooling step.

10 Claims, 3 Drawing Sheets

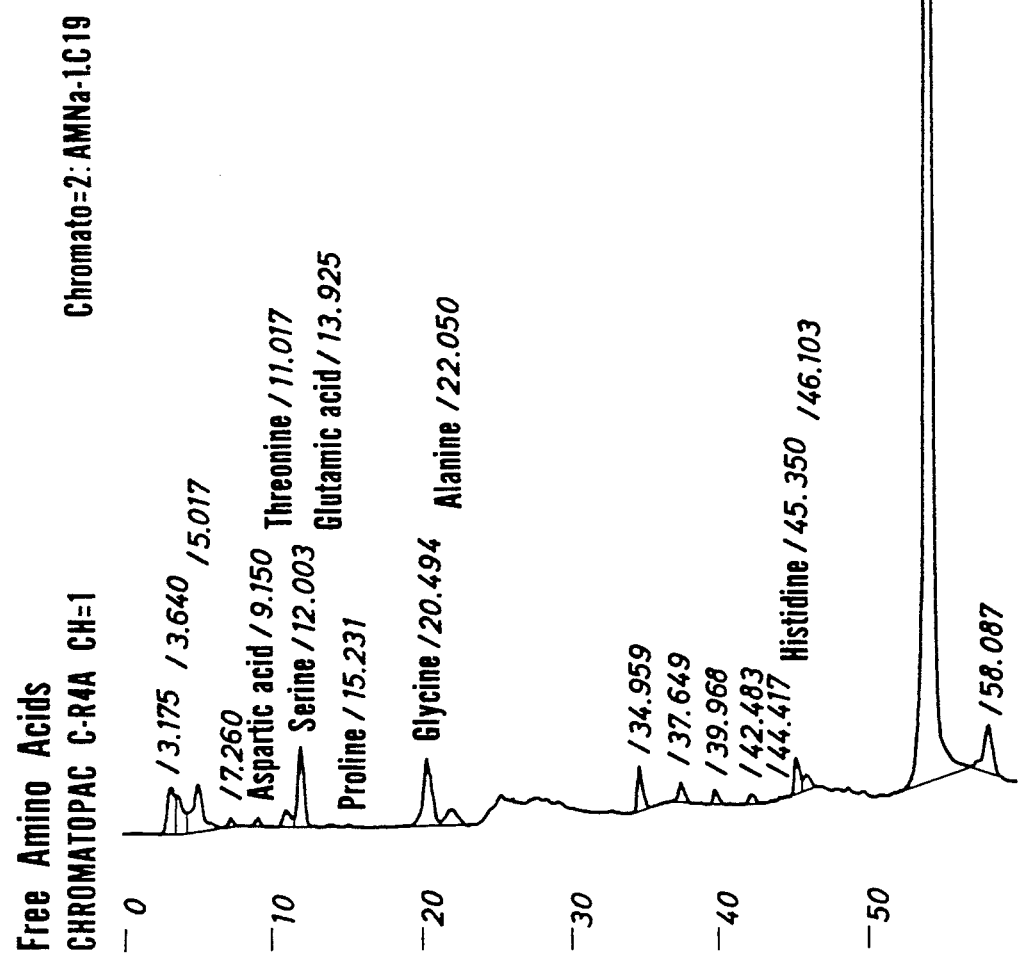

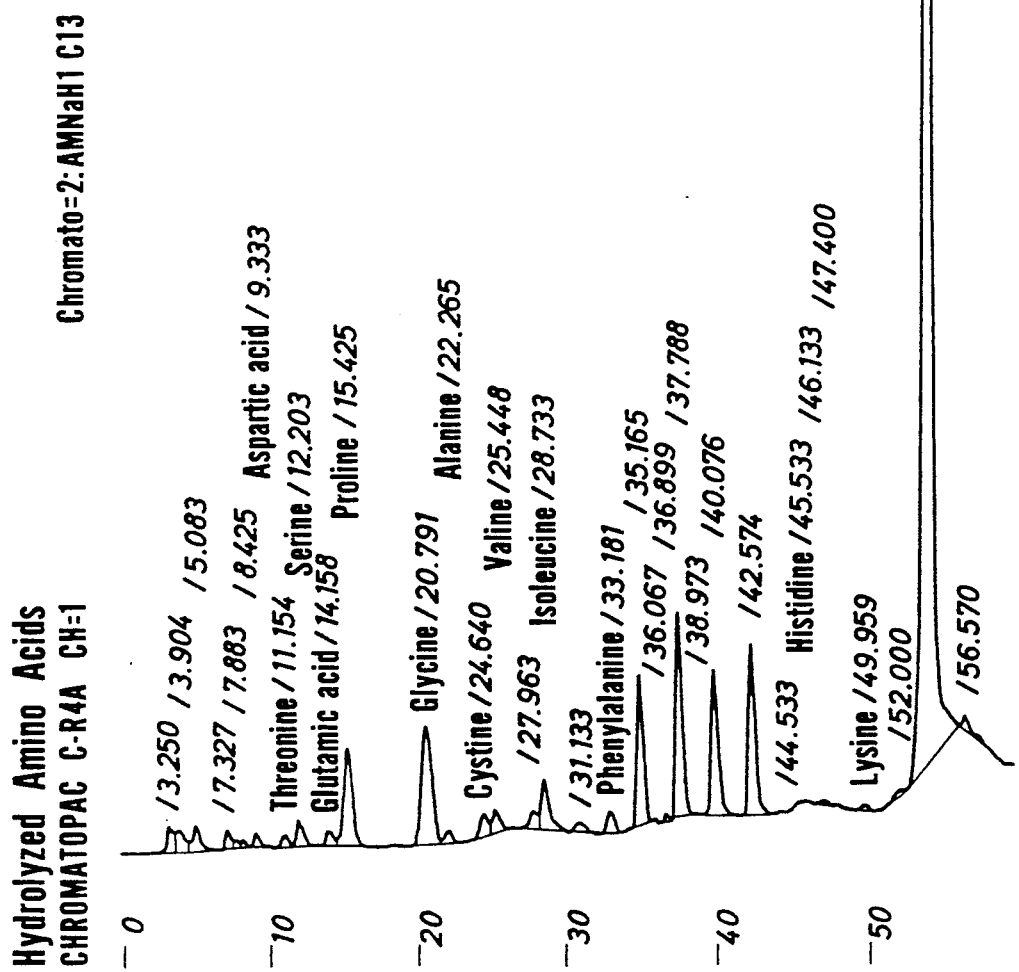

ACTIVE AMINO ACID CA, BEVERAGES CONTAINING SAME, AND PROCESS FOR THEIR PRODUCTION

BACKGROUND OF THE INVENTION

This invention relates to an active amino acid Ca product, i.e., a calcium oxide and/or calcium hydroxide product coexistent with a slight amount of one or more amino acids and hydrolyzable amino acid derivatives, beverages containing same, and a process for their production. More particularly, it relates to an active amino acid Ca of natural origin coexistent with a slight amount of one or more amino acids and hydrolyzable amino acid derivatives, which can be effectively absorbed into the human body and can deposit onto the bone with a high efficiency, beverages containing same, and a process for their production.

It has been widely accepted that calcium is an essential element for formation of bone or tooth of mammals as well as human beings. In addition, it has recently been found that calcium is one of the most important elements that support all sorts of life activities and, at present, calcium is receiving much attention in the front line of medical science.

It has been pointed out that deficiency of calcium induces not only osteoporosis but such diseases as hypertension, arteriosclerosis, arthralgia, diabetes, immunological diseases, and obesity ["Kurasi To Kenkou (Life and Health)", 1991, vol.9, published by Hoken Doujin Sha].

However, calcium can be absorbed only at an extremely low absorption ratio unless it is ingested together with vitamin D or proteins, and a necessary amount of calcium can not be absorbed by independent ingestion of calcium.

Recent study has revealed that an adult requires calcium in an amount of 600 mg per day. It is known, however, that calcium contained in foods or beverages is not completely absorbed by the body and that calcium content indicated for a particular food or beverage is greatly different from the amount of calcium actually absorbed therefrom by the body. Therefore, an enormous amount of calcium-containing foods must be ingested in order to take up the necessary amount of calcium from daily meals.

For example, calcium contained in cow's milk which is known as a drink containing calcium at a level as high as about 100 mg/100 ml and is believed to be absorbed with a high absorption ratio due to bonding of calcium to protein, can be absorbed at a level as low as 50% at the highest, i.e., 50 mg out of 100 mg. In addition, the protein bonding to calcium finally produces, after being digested and absorbed, lactic acid, butyric acid, pyroracemic acid, sulfuric acid and phosphoric acid, and most of 50 mg of the absorbed calcium is consumed for neutralizing these acids, thus the amount of calcium substantially absorbed being at most about 10 mg out of 100 ml of cow's milk.

Therefore, it is obvious that a necessary amount of calcium can not be ingested from cow's milk alone. However, in order to supply the deficient amount of calcium from other foods or beverages, even calcium-rich foods such as small dried sardines, sardines, cystophyllum fusiforme, toasted laver, etc. fail to supply the necessary amount of calcium. As a result, human beings are always in a calcium-deficient state, thus suffering from the aforesaid diseases induced by deficiency of calcium.

Such situation is not limited to Japan alone. In Europe and the United States where cow's milk is consumed 3 to 5 times as much as in Japan, incidence of osteoporosis which has been clarified to be induced by deficiency of calcium is twice that in Japan. This fact shows that calcium-rich foods or beverages such as cow's milk are insufficient to solve the problem of calcium deficiency.

Vitamin D known to accelerate absorption of calcium is produced from provitamin D in the body through irradiation with sunlight, or is ingested directly from foods. The thus ingested vitamin D is converted to active vitamin D by the action of accessory thyroid hormone. The active vitamin D helps calcium to be absorbed through intestinal wall The active vitamin D also causes calcium of the bone to be released from the bone in cooperation with the accessory thyroid hormone and, as a result, excess vitamin D is known to induce many troubles such as hypercalcemia, uremia, and malacosteon. Thus, in the USA, FDA does not approve vitamin D a medicine.

As has been described above, even cow's milk, which is believed to show the best calcium absorption ratio, permits calcium contained therein to be absorbed only in an extremely small absorption ratio and, therefore, it is at present extremely difficult to supply a necessary amount of calcium from foods alone. The calcium absorption ratio decreases with age of men or women. It has been clarified that all sorts of diseases and senility are mostly induced by deficiency of calcium from both the microscopic (or cell-level) and macroscopic (or general) points of view (Reports of the Japanese Society of Internal Medicine, Apr., 1990).

That is, when calcium level becomes lower than is necessary for maintaining life, a necessary amount of calcium is supplied from the bone, which in turn damages the bone cells, inducing retardation of growth of bone or tooth and osteoporosis. In addition, general health state will be damaged. For example, purification of blood and healthy state of brain, nerve, heart, muscle, etc. will not be maintained.

Of these diseases, osteoporosis is believed to be the disease to which human beings are most susceptible due to deficiency of calcium. In addition, this disease has been found to produce bedridden old men and old patients suffering from dementia. Thus, it is the most important subject to solve the problem of calcium deficiency for realizing healthy longevity in the coming aging society.

In order to solve the problem of calcium deficiency, calcium-containing products have been developed as nutrition-supplying foods, and calcium-containing preparations for medical use have been required to show higher absorption ratio ["Karusiumu No Subete (Everything on Calcium)" written by Takuo Fujita, issued by Aki Shobo].

Of the calcium-containing products, that one which has been developed by the inventors and which is a purified electrolysis product of oystershell contains more mineral ingredients and shows a higher calcium ion concentration. This electrolysis product has been proved to show a markedly high absorption ratio in the intestines and deposits on the bone in a markedly high ratio, and is now actively employed in many medical facilities including hospitals attached to university as nutrition-supplying food for prophylaxis and treatment of diseases of adults.

In the course of further investigations on the aforesaid calcium-containing product to develop a calcium product showing a higher absorption ratio and a higher deposition ratio on the bone, the inventors have found that a novel active amino acid calcium oxide and/or calcium hydroxide product coexistent with an extremely small amount of amino acids (particularly, low molecular weight amino acids) and hydrolyzable amino acid derivatives can solve the aforesaid problem, thus having completed the present invention.

SUMMARY OF THE INVENTION

It is an object of the present invention to provide the active amino acid calcium product of natural origin which is copresent with amino acids and/or hydrolyzable amino acid derivatives.

Another object of the present invention is to provide a process for producing the active amino acid calcium product of natural origin coexistent with amino acids and/or hydrolyzable amino acid derivatives, which comprises electrically calcining a calcium-containing natural material at 800° to 980° C. for 20 to 120 minutes in a calcining chamber free from oxygen, then forcibly cooling the product.

Other objects, features and advantages of the present invention will become apparent from the detailed description of the preferred embodiments of the invention to follow.

BRIEF DESCRIPTION OF THE DRAWINGS

FIG. 3 is a chart showing the results of quantitative analysis of free amino acids contained in the calcium oxide obtained in Example.

FIG. 4 is a chart showing the results of quantitative analysis of amino acids produced by hydrolysis of the sample.

In FIGS. 1 and 2, numeral 1 designates the apparatus, 2 a vacuum pump, 3 a $CO_2$ sensor, 4 heat-insulating members, 5 trays, 6 heaters, 7 an electrical heating furnace, 8 a heat control panel, and 9 a liquefied nitrogen gas bomb.

DETAILED DESCRIPTION OF THE PREFERRED EMBODIMENTS OF THE INVENTION

Figure 1:
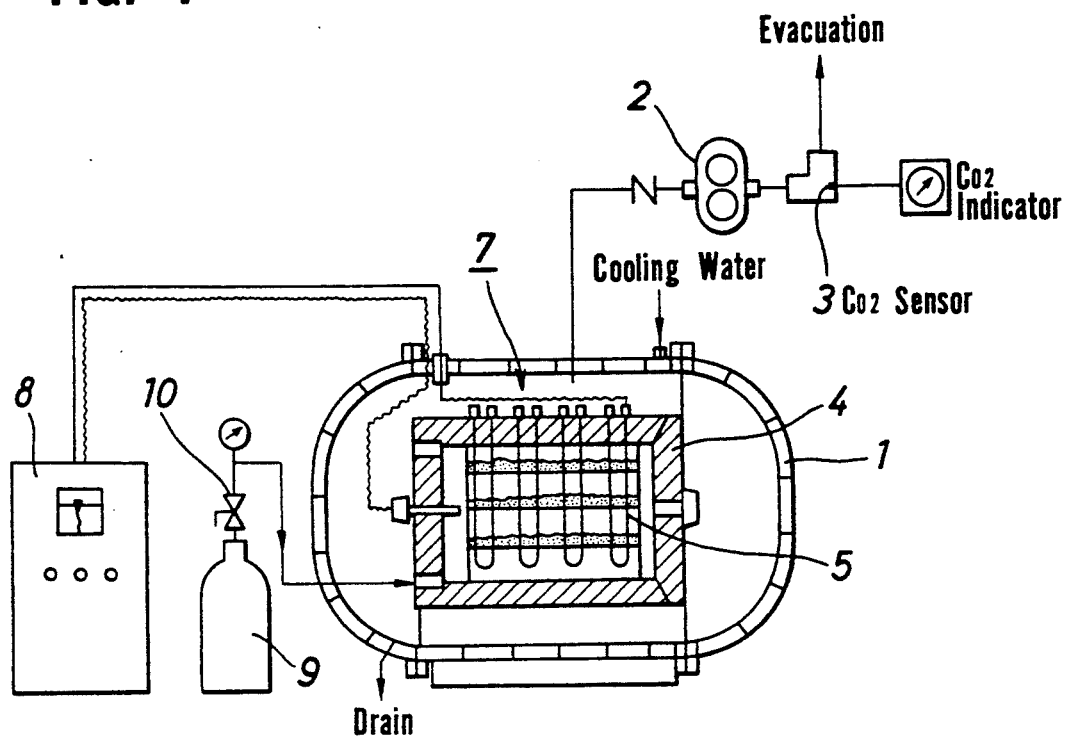
FIG. 1 is a vertical sectional view showing one embodiment of a batchwise apparatus for practicing the process of the invention.

The active amino acid calcium product has an important feature that amino acids, particularly low molecular weight amino acids, and/or hydrolyzable amino acid derivatives are copresent with calcium oxide and/or calcium hydroxide of natural origin.

The amino acids may form chelate bonds with calcium, or may coexist as hydrolyzable amino acid derivatives or in a free state. The amino acids can remain without being decomposed in the calcining step wherein amino acids might be decomposed at higher temperatures in the presence of oxygen.

The amino acids and hydrolyzable amino acid derivatives coexist in a slight amount and, as a general and non-limiting guide, they coexist in an amount of 0.0001 to 0.005% by weight, preferably 0.0005 to 0.008% by weight. Coexistence of the amino acids and/or the amino acid derivatives in such amount serves to improve calcium absorption ratio and deposition ratio on the bones as will become apparent from the test examples to be described hereinafter.

The amino acids confirmed by the inventors to coexist with the calcium oxide and/or calcium hydroxide of natural origin are as follows.

As amino acids produced by hydrolysis of the amino acid derivatives (e.g., peptides and proteins), there are illustrated aspartic acid, threonine, serine, glutamic acid, proline, glycine, alanine, cystine, valine, isoleucine, phenylalanine, histidine, lysine, and trace amounts of their derivatives and, as free amino acids, there are illustrated taurine, phosphoethanolamine, aspartic acid, threonine, serine, proline, glycine, alanine, phenylalanine, β-alanine, γ-aminobutyric acid, histidine, hydroxylysine, ornithine, and their derivatives.

These amino acids and the hydrolyzable amino acid derivatives may exist alone or as a mixture of two or more of them and, preferably, they exist as a mixture of two or more, preferably 10 or more, of them. Of the above-described amino acids, coexistence of a sulfur-containing amino acid of cystine serves to more markedly improve calcium absorption ratio in the intestines and deposition ratio onto the bones. Mechanisms of the cystine activity have not been clarified yet, but it may be presumed that the sulfur atom of cystine acts as a cross-linking agent between calcium and the amino acid, this cross-linking bond seemingly accelerating the absorption of calcium through the intestinal wall and deposition of calcium onto the bones.

In any case, such phenomenon has been found as experimental results in the course of the inventors' study, and it is quite a surprising fact that existence of a sulfur-containing amino acid as one of the amino acids coexistent with the active calcium oxide and/or calcium hydroxide product serves to more accelerate absorption of calcium through the intestinal wall and deposition thereof onto the bones.

It has been well known that calcium oxide is obtained by heat-treating calcium (calcium carbonate)-containing natural materials in the atmosphere according to the reaction represented by the following formula:

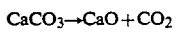

$$CaCO_3 \rightarrow CaO + CO_2$$

However, since this reaction is usually conducted in the atmosphere at a temperature as high as 1,000° to 1,400° C., the reaction becomes difficult to proceed as a partial pressure of $CO_2$ gas increases due to progress of the reaction, thus the heat treatment taking a prolonged time (about 2 hours). In addition, CaO is so unstable that it reacts with $CO_2$ in the atmosphere upon cooling to again form $CaCO_3$. It has been believed that organic ingredients attached or deposited to $CaCO_3$ are completely decomposed after the prolonged heat treatment at the elevated temperature.

It has been found for the first time by the inventors that the active amino acid product wherein amino acids and hydrolyzable amino acid derivatives contained in the raw material are not decomposed but remain and coexist therewith is obtained by calcining at a temperature lower than is employed in the prior art treatment in a calcining chamber free from oxygen. In addition, it has never been known and newly found by the inventors that copresence of amino acids and/or hydrolyzable amino acid derivatives in the calcined product serves to improve absorption of calcium through the intestinal paries and deposition of calcium onto the bones and that the absorption ratio and deposition ratio of calcium are more improved when a sulfur-containing amino acid is contained in the amino acids or the hydrolyzable amino acid derivatives.

The reason for the remaining and copresence of amino acids and/or hydrolyzable amino acid derivatives with the calcium oxide and/or calcium hydroxide may be presumed as follows. Namely, the amino acids partly form strong chelate bonds with calcium and, since the raw material is a natural substance, the calcium product does not have a uniform structure. For example, when a raw material of layered structure composed of many layer units such as oyster shell is used, amino acids and/or hydrolyzable amino acid derivatives depositing between the layers or bound to calcium through chelate bond are presumed not to be decomposed by the heat treatment but to remain coexistent with calcium oxide and/or calcium hydroxide.

In any case, the active amino acid calcium product shows excellent physical activities and shows markedly improved absorption ratio of calcium and deposition ratio onto the bones (remaining ratio in the body) in comparison with conventional calcium products.

Preparation of active calcium product

The active calcium product of the present invention is not limited as to process for its preparation. However, it is necessary to calcine the raw material under atmospheric pressure, reduced pressure or in vacuo at a temperature of 800° to 980° C., preferably 850° to 910° C., in calcining chamber free from oxygen. Though the reaction proceeds even at a temperature higher than 980° C., no additional merits are obtained, leading to mere waste of heat source. If the heating temperature is lower than 800° C., the active calcium product gradually blackens, resulting in a product of deteriorated quality.

Heating time varies depending upon the employed temperature, but is usually 20 to 120 minutes, preferably 30 to 60 minutes. After completion of the calcination, the product is forcibly cooled with a cooling gas such as an inert gas to effectively obtain the active amino acid calcium product.

As the inert gas to be used as a cooling gas, such inert gases as a nitrogen gas and a helium gas may be used, with a nitrogen gas being preferred.

By this process, the calcium contained in the raw material is converted to calcium oxide by the electrical heating and, upon discontinuation of the electrical heating, an inert gas is blown into the heating chamber to forcibly cool the produced calcium oxide to about ordinary temperature, thus the calcium product being obtained. This cooling method enables one to obtain a stable calcium oxide product without oxygen in the air being absorbed during the cooling step.

Illustrative of the calcium-containing natural materials are shells such as oystershell, Crustacea such as crab and lobster, algae such as *Cystophyllum fusiforme*, bones of mammals, and eggshell. Of these, oystershell is most preferable since it contains much amounts of calcium and amino acids (including sulfur-containing amino acids) and hydrolyzable amino acid derivatives and permits coexistence of amino acids with calcium due to its stratum structure.

On the other hand, calcium-containing mineral materials such as limestone and milk of lime yield calcium carbonate, calcium phosphate, calcium hydroxide, calcium lactate, and calcium gluconate as final products. These products show a low absorption ratio of calcium, and are utilized in the body only with a low ratio, thus not being used as the starting materials of the active amino acid calcium product of the present invention.

The active amino acid calcium product obtained by the present invention is an almost white powder and may be offered to consumers in the form of tablets prepared from the white powder according to conventionally known methods or in the form of beverages prepared by dissolving in an aqueous solution of various acids, particularly fermentation lactic acid, or in the form of Yoghurt or jelly.

Beverages containing the active amino acid calcium product of the present invention may be obtained by dissolving the active calcium product in an aqueous solution of an acid such as fermentation lactic acid, citric acid or malic acid. Of these, an aqueous solution of fermentation lactic acid is preferred from the viewpoint of the taste and solubility. In practice, the beverages may be obtained by dissolving about 0.5 to 2.4 g of the active calcium product powder per 100 cc of an about 10 to 35% by volume of fermentation lactic acid, preferably optically active L(+) lactic acid.

Figure 2:
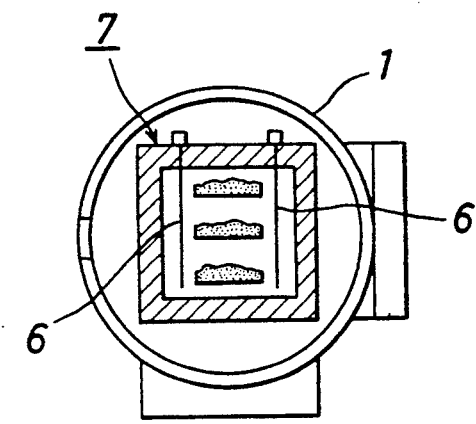
FIG. 2 is a side sectional view of the apparatus shown in FIG. 1.

The process of the present invention for producing the active calcium product is described below by reference to FIGS. 1 and 2 illustrating one embodiment of the apparatus for the production.

FIGS. 1 and 2 show a batchwise apparatus to be operated under reduced pressure or in vacuo for practicing the process of the present invention. However, the apparatus may be operated neither under reduced pressure nor in vacuo, and it suffices to purge the apparatus from oxygen upon calcination operation.

Apparatus 1 has a closed structure and is equipped with means to evacuate it if necessary. The evacuating means comprises a vacuum pump 2 and a $CO_2$ sensor 3 connected to each other through an evacuating pipe. Within the apparatus 1 is disposed an electrical heating furnace 7 having outer walls made of a heat insulation material 4, trays 5 for placing the raw material, and heaters 6 disposed along both sides of the trays. Numeral 8 designates a heat control panel for controlling the heater 6, and 9 designates an $N_2$ gas bomb for supplying an $N_2$ gas for cooling the heating furnace 7 connected to the furnace 7 through a valve 7.

The process for producing the active calcium product of the present invention using this apparatus is described below.

Calcium-containing natural raw materials such as shells, crustaceans, algae, bones, etc. are freed of impurities, ground to form particulate raw materials having a diameter of about 5 mm, and uniformly spread on the trays in a height of about 1 cm. Then, the door of the heating furnace 7 and the door of the apparatus 1 are successively closed and, if necessary, the vacuum pump 2 is operated to evacuate the apparatus to a degree of, for example, less than $2 \times 10^{-3}$ TORR, preferably $2 \times 10^{-2}$ TORR. Subsequently, the heater 6 is energized to initiate heating. Upon the temperature within the heating furnace 7 reaching about 600° C., monitoring of the $CO_2$ sensor is started. Heating is continued for 20 to 120 minutes, preferably 30 to 60 minutes, during which the temperature within the heating furnace is kept at 800° C. to 900° C., preferably 850° C. to 910° C. The rate of $CO_2$ generation reaches a maximum level when the temperature within the heating furnace 7 reaches about 800° C. and, after about 10 minutes, generation of the CO$_2$ gas is almost discontinued.

The reaction employed in the present invention may be carried out under atmospheric pressure if the reacting apparatus is operated after purging it of oxygen or, as is mentioned hereinbefore, may be conducted under reduced pressure or in vacuo. When the reaction is conducted under reduced pressure or in vacuo, the heating treatment is conducted at a degree of vacuum of less than $2 \times 10^{-1}$ TORR, preferably $2 \times 10^{-2}$ TORR, for 30 to 60 minutes. The reaction of CaCO$_3$→CaO + CO$_2$ rapidly proceeds even in vacuo to produce CaO containing only an extremely small amount of impurities. At this stage, operation of the heater 6 is discontinued, and a pressure-control valve 10 is opened to introduce a nitrogen gas into the heating furnace 7 to forcibly cool the produced calcium oxide to an ordinary temperature. After completion of the cooling, the vacuum pump 2 is stopped, and the whole procedures are completed when the pressure within the apparatus reaches atmospheric pressure.

The process of the present invention is described above by reference to the case of producing calcium oxide coexistent with amino acids and/or hydrolyzable amino acid derivatives and, in the case of producing an active calcium hydroxide product which is another embodiment of the present invention, hot calcium oxide after completion of the heating procedure is brought into water to cool, with the forcible cooling with a nitrogen gas being preferably conducted at the same time.

The reaction between calcium oxide and water easily takes place by forcibly bringing 40 to 50 cc, per 100 g of calcium oxide, of water to calcium oxide to yield calcium hydroxide. Needless to say, the thus produced calcium hydroxide is also coexistent with amino acids. This calcium oxide also shows a high absorption ratio into the human body and an excellent deposition ratio onto the bone similarly with the active calcium oxide product.

The present invention is now described in more detail by reference to the following Example.

Active calcium oxide product coexistent with amino acids and/or hydrolyzable amino acid derivatives was produced from oystershells using the apparatus shown by FIG. 1.

Firstly, the raw material of oystershells was well washed, and was completely freed of deposits by means of a brush. The oystershells were roughly ground to a size of about 10 to about 15 mm. About 50 g of the thus-ground oystershell product was placed in a ceramic crucible (8×8×4.5 cm) disposed in a closed vessel (made by Hayashi Denko Sha) within a Model K Kantal Super Electric Furnace. Thereafter, energization of the heater in the closed vessel was initiated under atmospheric pressure. 90 Minutes after the energization, the temperature within the vessel reached 850° C. Heating treatment was continued for 30 minutes at the temperature.

Subsequently, energization of the heater was discontinued and, at the same time, a nitrogen gas was introduced thereinto for 30 minutes to forcibly cool the calcium oxide product to an ordinary temperature.

100 g of the thus-obtained calcium oxide of oystershell origin was dissolved in 2 liters of a 10% hydrochloric acid aqueous solution. After adjusting pH of the solution to 4.0 with a 3N sodium hydroxide aqueous solution, the effective substance was adsorbed on 40 g of active carbon for use in column chromatography (60- to 150-mesh). The active carbon was collected by filtration, and well washed with pure water. The washed active carbon was subjected to elution with 2 liters of a 0.1N hydrochloric acid solution in 50% aqueous methanol for 8 hours, followed by filtration to remove the active carbon. The 0.1N hydrochloric acid solution in 50% aqueous methanol was concentrated by means of an evaporator to obtain 200 mg of the effective substance.

Then, the effective substance was subjected to gel permeation chromatography using Sephadex G-50(product of Pharmacia Japan) as follows. That is, a glass tube of 25 mm in inside diameter and 500 mm in height was packed with well swollen and degased Sephadex G-50 to the height of 450 mm. 200 mg of the effective substance was dissolved in 5 ml of pure water and was subjected to gel permeation chromatography over the Sephadex column using pure water as an eluent at a flow rate of 5 ml/h. Thus, the effective substance was collected as fraction Nos. 45 to 60. The effective substance was detected using UV rays of 260 nm in wavelength. The contents of fraction Nos. 45 to 60 were combined and concentrated to dryness to obtain 100 mg of a powdery product.

Quantitative analysis of free amino acids and hydrolyzable amino acid derivatives contained in the effective substance gave the results shown in FIGS. 3 and 4.

Analysis Item: Quantitative analysis of free amino acids and hydrolyzable amino acid derivatives contained in the sample Analyzer: Shimazu high-speed liquid chromatograph (Amino acid-analyzing system)

Analysis Results: presented in terms of the unit of "nmol/mg" based on retention times

[Results of the analysis]

1. Conditions for HPLC analysis

Column: Shim-pack ISC-07/S1504 Na (4.0 mm I.D.×150 mm L.)

Top column: Shim-pack ISC-30/S0504 Na (4.0 mm I.D.×150 mm L.)

Mobile phase:
 A; 0.20N sodium citrate buffer solution (pH 3.2)(containing 7% ethanol)
 B; 0.60N sodium citrate buffer solution (pH 10.0)
 C; 0.20N sodium hydroxide
 Multistage gradient elution Flow rate: 0.3 ml/min Column temperature: 55° C.

Detection: by converting to OPA derivative at post-column stage

Reacting reagents:
 solution A; commercially available 0.04 % sodium hypochlorite aqueous solution
 solution B; o-phthalaldehyde solution containing
  0.08% o-phthalaldehyde,
  1.40% ethanol,
  0.04% polyoxyethylene lauryl ether, and
  0.10% solution of N-acetylcysteine in a carbonate-borate buffer Flow rate of reagents: 0.3 ml/min each Detector: Fluorescence detector (Ex=348 nm; Em=450 nm)

Sensitivity: 1 V Integrator terminal Sensitivity=LOW

Chart speed: 2 mm/min

Injected aount:

standard solution 10 µl
sample solution 20 µl

2. Preparation of standard solution

The standard solution was prepared by adding tryptophane to a standard amino mixture solution (type II; made by Wako Junyaku Co., Ltd.) and diluting the solution with a 0.2N sodium citrate buffer solution (pH 2.2) to adjust the concentration to 100 nmol/ml.

3. Preparation of sample solution (1) Free amino acids 19.6 mg of a sample was dissolved in 5 ml of a 0.2N sodium citrate buffer solution (pH 2.2), then filtered through a 0.45-µm membrane filter.

(2) Amino acids obtained by hydrolysis of hydrolyzable amino acid derivatives

To 14.6 mg of a sample was added 1 ml of 20% hydrochloric acid and, after sealing the tube under reduced pressure, placed in a thermostatic chamber at 110° C. for 22 hours to conduct hydrolysis. After allowing the tube to cool, the sample was concentrated to dryness in a rotary evaporator, followed by adding thereto a 0.2N citrate buffer solution (2.2) to make the total volume 5 ml. The resulting solution was filtered through a 0.45-µm membrane filter.

Evaluation of the active calcium product on absorption properties and properties of remaining in the human body The active calcium product obtained in the foregoing Example was tested as follows with respect to the absorption properties and the properties of remaining in the human body.

Test place: the Kobe University, Third Internal Department, Room of Professor, M. D. Takuo Fujita
Testers: Prof. Takuo Fujita, Yosio Yoshimoto, Masaaki Fukase, and Tatsuo Tsukamoto
Object of the test:
The test was conducted for examining the degree of absorption through the intestinal wall, i.e., the degree of biological utility, which is most important with calcium preparations or calcium-containing foods. Thus, metabolic equilibrium test was conducted in the following manner by cooperation with four test subjects. Calcium contents of the foods they ate, and feces and urine they produced for a predetermined period of time were analyzed for the object.
Analyzing method:
The metabolic equilibrium test was conducted as follows. That is, four test subjects were supplied with predetermined foods and calcium product of the present invention, calcium carbonate or calcium lactate (600 mg in terms of calcium) in the order of 5 days for control, 2 days of intermission, 5 days for the product of the present invention, 2 days of intermission, and 5 days for mineral calcium carbonate or calcium lactate.
Results:
As is shown in Table 1, the calcium product of the present invention was found to more remain in the body in comparison with the control period, thus causing a positive calcium balance. On the other hand, calcium carbonate was found to remain in a less amount, and calcium lactate in a much less amount. As is shown in Table 2, the product of the present invention showed the highest remaining ratio, with calcium carbonate being next.

Conclusions:
The preliminary tests revealed that the product of the present invention tends to be absorbed and remain in the body more than calcium carbonate and calcium lactate.

TABLE 1

| | Calcium Balance (mg/day) | | | | |
|---|---|---|---|---|---|
| | Case 1 | Case 2 | Case 3 | Case 4 | Mean ± SEM |
| Control | −118 | −5 | −200 | −22 | −78 ± 52 |
| Product of the invention | +478 | +341 | −199 | +256 | +219 ± 146 |
| Calcium carbonate | −149 | −60 | | | −104 ± 44 |
| Calcium lactate | | | −480 | −85 | −283 ± 197 |

Notes:
Case 1: 69-year old healthy female
Case 2: 74-year old healthy male
Case 3: 69-year old healthy female
Case 4: 86-year old healthy male

TABLE 2

| Remaining Ratio | |
|---|---|
| | Remaining Ratio* |
| Product of the invention | 49 ± 15 |
| Calcium carbonate | 22 ± 2 |
| Calcium lactate | 12 ± 2 |

*1 − (Increase in excreta amount/Increase in intake) × 100

According to the process of the present invention wherein calcination is conducted with shutting the calcination chamber from oxygen, amino acids of raw material origin remain as trace-amount ingredients without being decomposed. In addition, since cooling after the calcination is forcibly conducted using a nitrogen gas with shutting the apparatus from oxygen, reactions with $CO_2$ and $O_2$ are avoided, which serves to provide calcium oxide and calcium hydroxide coexistent with amino acids.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. An active amino acid calcium product comprising calcium of oyster shell origin in a layered structure and in a form selected from the group consisting of the oxide and the hydroxide, and one or more compounds selected from the group consisting of amino acids and hydrolyzable amino acid derivatives, including cystine, in an amount of 0.001 to 0.05% by weight, said compound being intimately coexistent with said calcium by being between layers of said layered structure of calcium or bound to said calcium.

2. The active amino acid calcium product as set forth in claim 1, wherein said hydrolyzable amino acid derivatives yield, after hydrolysis, one or more of amino acids selected from the group consisting of aspartic acid, threonine, serine, glutamic acid, proline, glycine, alanine, valine, isoleucine, phenylalanine, histidine, lysine, and the derivatives thereof.

3. The active amino acid calcium product as set forth in claim 1, wherein said amino acids include cystine and one or more of hydrolyzable amino acid derivatives yielding, after hydrolysis, amino acids selected from the group consisting of aspartic acid, threonine, serine, glutamic acid, proline, glycine, alanine, valine, isoleucine, phenylalanine, histidine, lysine, and the derivatives thereof.

4. The active amino acid calcium product as set forth in claim 1, wherein said amino acids include one or more of free amino acids selected from the group consisting of taurine, phosphoethanolamine, aspartic acid, threonine, serine, proline, lycine, alanine, pheylalanine, $\beta$-alanine, $\gamma$-aminobutyric acid, histidine, hydroxylysine, ornithine, and the derivatives thereof.

5. A beverage containing the active amino acid calcium product, which is produced by dissolving the active calcium product described in one of claims 1, 2, 4, 5 or 6 in an aqueous solution of fermentation lactic acid.

6. A process for producing an active amino acid calcium product wherein a member selected from the group consisting of calcium oxide and calcium hydroxide of oyster shell origin is intimately coexistent with one or more amino acids and hydrolyzable amino acid derivatives, which process comprises electrically heating roughly ground oyster shell to 800° to 980° C. for 20 to 120 minutes in a calcining chamber free from oxygen and under reduced pressure or in vacuo, and forcibly cooling the calcined product.

7. The process for producing an active amino acid calcium product as set forth in claim 6, wherein said amino acids include cystine.

8. The process for producing an active amino acid calcium product as set forth in claim 6, wherein said hydrolyzable amino acid derivatives yield, after hydrolysis, one or more of amino acids selected from the group consisting of aspartic acid, threonine, serine, glutamic acid, proline, glycine, alanine, valine, isoleucine, phenylalanine, histidine, lysine, and the derivatives thereof.

9. The process for producing an active amino acid calcium product as set forth in claim 6, wherein said amino acids include cystine, and one or more of hydrolyzable amino acid derivatives yielding, after hydrolysis, amino acids selected from the group consisting of aspartic acid, threonine, serine, glutamic acid, proline, glycine, alanine, valine, isoleucine, phenylalanine, histidine, lysine, and the derivatives thereof.

10. The process for producing an active amino acid calcium product as set forth in claim 6, wherein said amino acids include one or more of free amino acids selected from the group consisting of taurine, phosphoethanolamine, aspartic acid, threonine, serine, proline, lysine, alanine, phenylalanine, $\beta$-alanine, $\gamma$-aminobutyric acid, histidine, hydroxylysine, ornithine, and the derivatives thereof.

* * * * *

UNITED STATES PATENT AND TRADEMARK OFFICE
CERTIFICATE OF CORRECTION

PATENT NO.    :   5,296,246
DATED         :   March 22, 1994
INVENTOR(S)   :   INOUE et al.

It is certified that error appears in the above-identified patent and that said Letters Patent is hereby corrected as shown below:

On the cover page, Item [30], "August 9, 1991" should be --August 8, 1991--.

Signed and Sealed this

Thirtieth Day of August, 1994

Attest:

BRUCE LEHMAN

Attesting Officer

Commissioner of Patents and Trademarks